United States Patent
Jarvis et al.

Patent Number: 5,437,860
Date of Patent: Aug. 1, 1995

[54] SKIN AND SCALP BARRIER FOR USE WITH HAIR TREATMENT PRODUCTS

[75] Inventors: David P. Jarvis, Midway; Mario J. de la Guardia; Joseph Jones, Jr., both of Savannah, all of Ga.

[73] Assignee: Aminco, Inc., Wilmington, Del.

[21] Appl. No.: 79,809

[22] Filed: Jun. 22, 1993

[51] Int. Cl.⁶ .................. A45D 7/04; A61K 7/09; A61K 7/40
[52] U.S. Cl. .................. 424/70.2; 132/202; 132/205; 424/70.1
[58] Field of Search .............. 424/71, 70.1, 70.2; 132/202, 205

[56] References Cited
U.S. PATENT DOCUMENTS
4,592,908  6/1986  Wajaroff et al. .................. 424/71

Primary Examiner—Melvyn I. Marquis
Assistant Examiner—Robert H. Harrison
Attorney, Agent, or Firm—Nikaido, Marmelstein, Murray & Oram

[57] ABSTRACT

Compositions for the protection of skin and scalp during hair relaxer treatment. Also disclosed are processes for producing said compositions, and methods of using said compositions during hair relaxer treatment. The compositions of the invention protect the scalp from the irritating side effects of hair relaxers, but do not interfere with the straightening activity of the hair relaxers. The compositions of the invention comprise paraffin and a paraffin miscible ester.

2 Claims, 1 Drawing Sheet

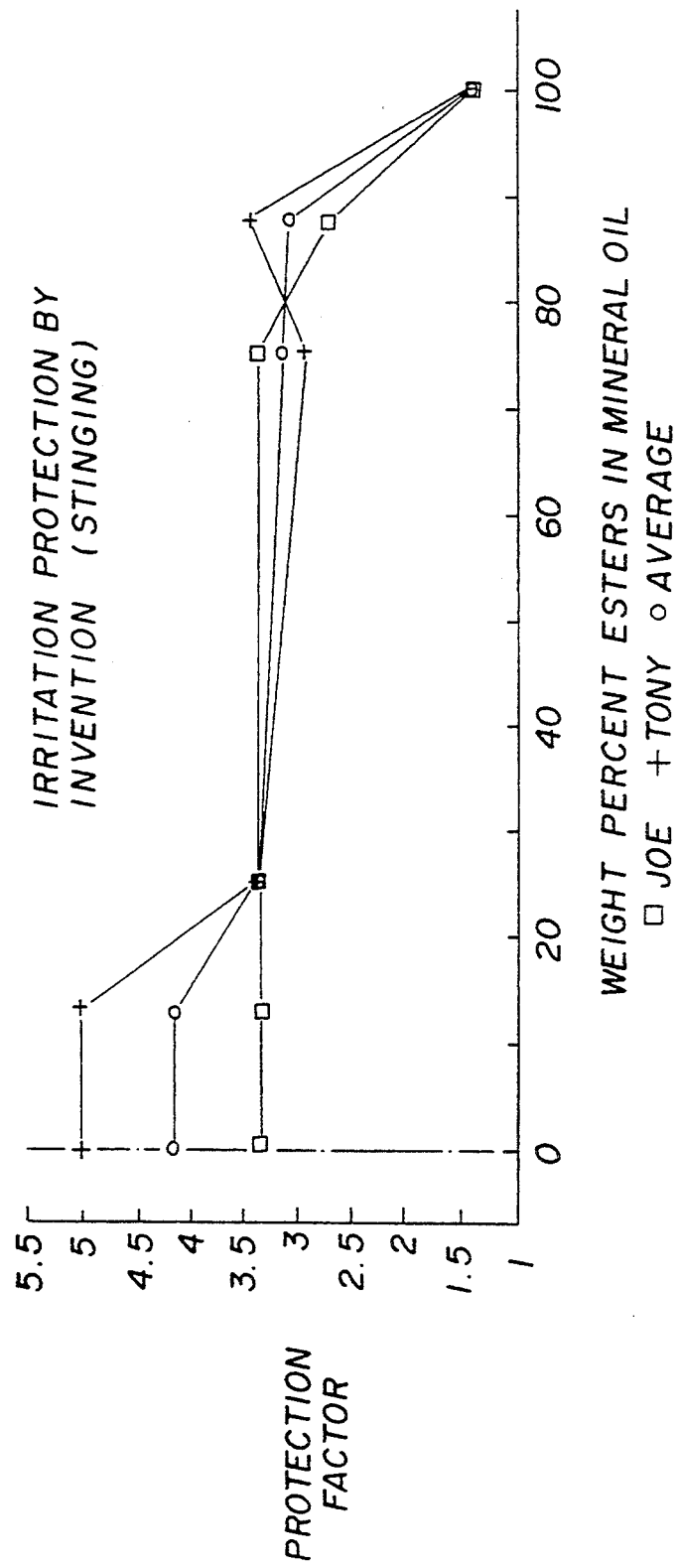

SKIN AND SCALP BARRIER FOR USE WITH HAIR TREATMENT PRODUCTS

BACKGROUND OF THE INVENTION

This invention relates to compositions for protecting scalp when undergoing straightening or relaxing of hair. In particular, the compositions of the present invention block the skin irritation side effects of the highly alkaline hair relaxers, but do not interfere with the straightening action of the relaxer on the hair.

BACKGROUND INFORMATION

Aqueous highly alkaline hair relaxing or straightening compositions are known in the art. These compositions usually have a highly alkaline pH of about 12 to about 14 due to the presence of an alkaline material such as water-soluble alkali or alkaline earth hydroxide or an organic chemical base such as guanidine, guanidine hydroxide or quaternary ammonium hydroxide. These products, although very effective, are irritating to the skin and scalp, and are often used with a protective barrier or base such as mineral oil or petrolatum applied to the scalp prior to the application of the hair relaxer.

Also available are highly alkaline hair relaxers of the type commonly called "no-base" hair relaxers. Even though the products are called "no-base" a small amount of the barrier compound must also be used with such products, i.e., the hairline and ears are coated with a protective oleaginous base such as petrolatum, mineral oil or lanolin, before applying the highly alkaline hair relaxer. One type of no-base hair relaxer formulation contains as the active hair straightening agent an alkali metal hydroxide, typically a caustic base, such as sodium hydroxide or potassium hydroxide. When a relatively low active level of about 1.5 to about 2.5 weight percent of caustic base is used, the protective base is applied only to the hairline to protect the skin around the forehead, ears and neckline. Such no-base formulations preferably have some of the protective oleaginous material emulsified in an aqueous composition, and are supplied in a single product kit.

A preferred and more recently developed type of no-base hair relaxer formulation is commonly called a "no-lye" hair relaxer. For some users a protective base need not be applied to the scalp and may need not be applied to the hairline with a no-base, no-lye relaxer. The term "no-lye" means that the active hair straightening agent is not NaOH or KOH. In commercial practice, the relatively strong organic chemical base, guanidine is usually present in the form of guanidine hydroxide. However, guanidine hydroxide is not generally stable for long periods in aqueous solutions. Consequently, it must be prepared fresh just before using.

Also available are more stable formulations of the no-base, no-lye type hair relaxers, and these are prepared using LiOH.

Because the prior art barrier or base compounds interfere with the straightening action of the relaxer if they coat the hair shaft, the application of the barrier or base is a very tedious and time consuming process. This process involves separating the hair into very small segments to apply the compositions only to the skin and scalp and not to the hair itself.

SUMMARY OF THE INVENTION

The present inventors have discovered that a composition comprising mostly paraffin and a paraffin miscible, ion-permeable ester blocks the skin irritation side effects of the highly alkaline hair relaxers when a light coating of the gel is applied to the skin or scalp prior to applying the relaxer cream. Surprisingly, the ester composition does not interfere with the action of the relaxer on the hair. The present invention, therefore, involves a method of relaxing hair with the additional component of the skin and scalp barrier composition that allows rapid application of the materials to the head and very thorough action of the relaxer on the hair.

BRIEF DESCRIPTION OF THE DRAWING

FIG. 1 shows how the RPF is affected as the percentages of Dioctyl Maleate in Mineral Oil are changed.

DETAILED DESCRIPTION OF THE INVENTION

The principal components of the compositions of the invention are paraffin and an ester. The compositions comprise about 10-85 weight percent paraffin and about 15-90 weight percent paraffin-miscible and ion permeable esters. The resulting composition may be a gel or a liquid. The viscosity of the composition may be altered as desired by the addition of a thickener such as Cab-O-Sil ® (fumed silica).

Other components that can be added to the compositions of the present invention include fragrances, preservatives and other conventional hair care adjuvants.

The paraffin may be of two general types: liquid paraffin or mineral oil; or white soft paraffin, yellow soft paraffin, or petrolatum. These components are known to those skilled in the art and are available commercially.

The esters usable in the present invention are selected from the Cosmetics, Toiletries, and Fragrance Association, Inc., (CTFA) approved esters which, when mixed with the paraffin of the present invention, produce a composition which has the properties of the present invention. Preferred esters are esters with the formula

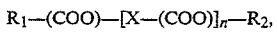

$$R_1-(COO)-[X-(COO)]_n-R_2,$$

wherein n is 0, 1, or 2;
wherein $R_1$ is selected from the group consisting of $C_1$–$C_{30}$ alkyl, $C_1C_1$–$C_{30}$ alkene, phenyl, benzyl, polyhydroxy $C_1$–$C_{30}$ alkanols, $C_1$–$C_5$ amino acid, $C_1$–$C_{30}$ alkylamine, $C_1$–$C_{30}$ oxy-alcohol; wherein X is selected from the group consisting of a single bond, $C_1$–$C_{30}$ alkyl, $C_1$–$C_{30}$ alkene, $C_1$–$C_{30}$ alkyl-oxy $C_1$–$C_{30}$ alkyl, $C_1$–$C_{30}$ alkylcarboxy $C_1$–$C_{30}$ alkyl, phenyl, phenyl $C_1$–$C_{30}$ alkyl, and wherein $R_2$ is defined the same as $R_1$, and $R_1$ and $R_2$ may be the same or may be different.

Most preferred esters are those wherein $R_1$ and $R_2$ are each $C_4$–$C_{20}$, especially $C_6$–$C_{10}$, alkyl groups and where n=1 or 2. The most particularly preferred ester is dioctyl maleate. Specific esters which can be used in the present invention include acetylated glycol stearate, acetylated sucrose distearate, acetyl tributyl citrate, acetyl triethyl citrate, acetyl trioctyl citrate, amyl acetate, ascorbyl dipalmitate, ascorbyl palmitate, ascorbyl stearate, benzyl acetate, benzyl benzoate, benzyl cinnamate, butyl acetate, butyl acetyl ricinoleate, butyl myristate, butyl oleate, butyl stearate, C18-36 acid glycol ester, C12-15 alcohols benzoate, C12-15 alcohols lactate, C12-15 alcohols octanoate, C18-20 glycol isostearate, C14-16 glycol palmitate, C11-15 pareth-3 oleate, C11-15 pareth-3 stearate, C11-15 pareth-12 stearate, C12-15 pareth-9 hydrogenated tallowate, C12-15 pareth-12 oleate, cetearyl isononanoate, cetearyl octanoate, cetearyl palmitate, cetyl acetate, cetyl lactate, cetyl myristate, cetyl octanoate, cetyl palmitate, cetyl ricinoleate, cetyl stearate, decyl isostearate, decyl oleate, decyl succinate, dibutyl adipate, dibutyl phthalate, dibutyl sebacate, Di-C12-15 alcohols adipate, dicapryl adipate, dicetyl adipate, diethoxyethyl succinate, diethylaminoethyl stearate, diethyl aspartate, diethylene glycol dibenzoate, diethyl glutamate, diethyl phthalate, diethyl sebacate, dihexyl adipate, diisobutyl adipate, diisocetyl adipate, diisodecyl adipate, diisopropyl adipate, diisopropyl diinoleate, diisopropyl sebacate, diisostearyl adipate, diisostearyl diinoleate, diisostearyl malate, dilauryl citrate, dimethyl phthalate, dioctyl adipate, dioctyl diinoleate, dioctyl maleate, dioctyl phthalate, dioctyl sebacate, dioctyl succinate, dipropylene glycol dibenzoate, dipropylene glycol salicylate, ditridecyl adipate, ditridecyl diinoleate, ethoxydiglycol acetate, ethoxyethanol acetate, ethyl acetate, ethyl glutamate, ethyl laurate, ethyl linoleate, ethyl myristate, ethyl palmitate, glycol dioctanoate, glycol distearate, glycol hydroxystearate, glycol oleate, glycol stearate, glycol stearate SE, hexanediol distearate, hexyl laurate, isoamyl acetate, isoamyl laurate, isobutyl acetate, isobutyl myristate, isobutyl palmitate, isobutyl pelargonate, isobutyl stearate, isoceteareth-8 stearate, isoceteth-10 stearate, isocetyl isodecanoate, isocetyl palmitate, isocetyl stearate, isocetyl stearoyl stearate, isodecyl laurate, isodecyl myristate, isodecyl neopentanoate, isodecyl oleate, isodecyl palmitate, isohexyl laurate, isohexyl palmitate, isononyl isononanoate, isopropyl acetate, isopropyl laurate, isopropyl linoleate, isopropyl myristate, isopropyl oleate, isopropyl palmitate, isopropyl sorbate, isopropyl stearate, isopropyl tallowate, isostearyl benzoate, isostearyl isostearate, isostearyl lactate, isostearyl neopentanoate, isostearyl palmitate, isostearyl stearoyl stearate, laureth-2 benzoate, laureth-6 citrate, lauryl isostearate, lauryl lactate, lauryl methacrylate, lauryl myristate, lauryl palmitate, lauryl stearate, methyl acetate, methyl caproate, methyl caprylate, methyl caprylate/caprate, methyl cocoate, methyl glucose sesquioleate, methyl glucose sesquistearate, methyl hydroxystearate, methyl laurate, methyl linoleate, methyl myristate, methyl oleate, methyl palmitate, methyl pelargonate, methyl stearate, myristyl lactate, myristyl myristate, myristyl neopentanoate, myristyl propionate, myristyl stearate, nonyl acetate, octyl myristate, octyl palmitate, octyl pelargonate, octyl stearate, oleyl acetate, oleyl linoleate, oleyl myristate, oleyl oleate, oleyl stearate, propylene glycol isostearate, propyl acetate, propylene carbonate, propylene glycol dicaprylate, propylene glycol dicocoate, propylene glycol diisonananoate, propylene glycol dilaurate, propylene dioctanoate, propylene glycol dipelargonate, propylene glycol distearate, propylene glycol laurate, propylene glycol myristate, propylene glycol oleate, propylene glycol stearate, stearyl acetate, stearyl caprylate, stearyl citrate, stearyl heptanoate, stearyl lactate, stearyl octanoate, stearyl stearate, sucrose acetate isobutyrate, sucrose benzoate, sucrose distearate, sucrose laurate, sucrose stearate, tributyl citrate, tridecyl stearate, triethyl citrate, triisocetyl citrate, triisopropyl trilinoleate, trilauryl citrate, trimethylopropane triisostearate, trimethylolpropane trioctanoate, trioctyl citrate, and tristearyl citrate. These esters are known to those skilled in the art and are commercially available.

The compounds of the present invention are made by mixing together the ingredients, typically with heating and agitation, by methods known to those skilled in the art.

The compositions of the invention are applied to the scalp, skin, and generally some hair prior to the application of the relaxer. The compositions of the present invention may be used with different types of hair relaxer products including lye-type, no-base, and no-base, no-lye type. The compositions of the present invention have been tested against commercial products including DARK AND LOVELY/BEAUTIFUL BEGINNINGS® (Guanidine Ohio), PERFECTLY YOURS® (LiOH), and REALISTIC® (NaOH) relaxers.

The particular advantage of the compositions of the present invention over the prior art skin barrier products, such as mineral oil or petrolatum, is that the compositions of the present invention surprisingly do not interfere with the relaxing action of hair relaxers. The application of the hair relaxers is therefore far less tedious and time-consuming. In the prior art methods of applying the barrier product, the product had to be carefully applied to the scalp by parting the hair many times and applying the barrier on the scalp at the base of each part. If the person applying the barrier did not cover the scalp completely, the person undergoing the hair straightening treatmetn would experience mild to severe stinging and burning. If the person applying the barrier allowed the barrier to cover the hair near the scalp, the hair that was covered by the barrier would not be relaxed. Thus, the entire hair relaxing process was very time consuming and possibly quite uncomfortable for the person undergoing the treatment. By using the present invention however, the barrier can be applied very generally and the barrier will 1) protect the skin and scalp, and 2) not interfere with the relaxation of the hair.

While not wishing to be restricted in any way, the present inventors believe that the compositions of the present invention increase the lipid-like character of the skin and are substantive with the skin. This interaction with the skin is believed to cause the skin to be more ion repellant and therefore less irritated by the highly alkaline relaxers. Because the hair does not have lipid properties, the compositions do not become substantive with the hair and the compositions therefore do not interfere with the action of the relaxers on the hair itself.

EXAMPLE 1

A barrier gel was made by mixing the following.

| GEL #1 | % (w/w) |
| --- | --- |
| Mineral oil | 55 |
| Dioctyl Maleate | 40 |
| Fumed Silica | 5 |
|  | 100 |

In a vessel outfitted with a high-shear stirrer, mix the mineral oil and ester components while heating slowly to 60°–65° C. Begin high-shear mixing and slowly add the fumed silica component. When fumed silica addition is complete; mix under high-shear for 30 minutes, then cool to room temperature.

EXAMPLE 2

A barrier gel was made as follows.

| GEL #2 | % (w/w) |
|---|---|
| Thickened Mineral oil | 40 |
| Sold as PENRECO GEAHLENE 750, "Mineral Oil (and) Hydrogenated Butylene/Ethylene/Styrene Copolymer (and) Hydrogenated Ethylene/Propylene/Styrene Copolymer" | |
| Mineral oil | 14 |
| Dioctyl Maleate | 40 |
| Isopropyl Myristate | 2 |
| Fumed Silica | 4 |
| | 100 |

The above product was made by the same method as Example 1.

EXAMPLE 3

A barrier liquid was made as follows.

| LIQUID #3 | Parts | | | | | |
|---|---|---|---|---|---|---|
| Mineral oil | 100 | 87.5 | 75 | 25 | 12.5 | 0 |
| Dioctyl Maleate | 0 | 12.5 | 25 | 75 | 87.5 | 100 |

Blend components by stirring. (Note-some esters may require mild to moderate heating to hasten their dissolution in mineral oil.)

EXAMPLE 4

A composition using 10% petrolatum and 90% -FIN-SOLV TN® (commercial mixture of benzoate esters of C-12 to C-15 alcohols) may be prepared. The mixture is a slightly viscous, pourable liquid.

| Formula #407 | % |
|---|---|
| Part A | |
| Bernel Ester DOM | 40.00 |
| Light Mineral oil | 11.60 |
| Part B | |
| Vigilan | 0.75 |
| Lecithin | 0.50 |
| Abil AV-20 | 0.35 |
| Vitamin A Palmitate | 0.075 |
| Vitamin E Acetate | 0.03 |
| IPM | 2.00 |
| Tenox 6 | 0.00075 |
| Aloe Vera Lipo Quinone | 0.10 |
| Part C | |
| Crotein IP | 0.10 |
| Fragrance MF2971 | 0.10 |
| Butyl Parabene | 0.09 |
| Part D | |
| Cab-o-sil | 4.00 |
| Pennzoil #514-44-CC-7 | 40.00 |
| TOTAL | 100.00 |

EXAMPLE 6

Procedure for Skin Irritation Evaluation

Using a template, mark off several one-inch-square areas of the forearm.

To establish the unprotected "sting/burn time" ($T_{un}$) apply a thin layer of a hair relaxer compositon so that it covers one of the marked areas. Start a timer and note the time that a stinging or burning sensation is first felt (stinging is defined as a sharp pain resembling a pin prick or insect bite, and burning is defined as a strong sensation of heat). Remove the relaxer by rinsing and wash the area thoroughly with a mild acidic surfactant (e.g., relaxer neutralizing shampoo).

To determine the protected "sting/burn time" ($T_p$)., apply two drops of the protectant to be tested as an even coating to one of the test areas, then apply the same hair relaxer cream as above. Record the time of the first occurrence of stinging or burning. Remove the relaxer by rinsing and wash the area thoroughly, with the mild acidic surfactant.

The degree of protection against chemical irritation, e.g., the Relaxer Protection Factor (RPF) provided by the protectant is calculated as follows;

$RPF = T_p/T_{un}$

Table 1 below and FIG. 1 show how the RPF is affected as the percentage of Dioctyl Maleate is changed. The other component is mineral oil.

TABLE 1

| | J. | | T. | | Average |
|---|---|---|---|---|---|
| ester % | J-Tp | J-RPF | T-Tp | T-RPF | A-RPF |
| 0 | 50 | 3.33 | 50 | 5 | 4.17 |
| 12.5 | 50 | 3.33 | 50 | 5 | 4.17 |
| 25 | 50 | 3.33 | 34 | 3.4 | 3.37 |
| 75 | 50 | 3.33 | 29 | 2.9 | 3.12 |
| 87.5 | 40 | 2.67 | 34 | 3.4 | 3.03 |
| 100 | 20 | 1.33 | 14 | 1.4 | 1.37 |

EXAMPLE 7

Briefly, this test involved applying a thin film of barrier material onto each forearm and applying an irritant on top of the barrier film. With time zero being the time the irritant was applied, the elapsed time was recorded for each of the following sensations, itching, stinging, and burning. Table 2 contains the data I obtained from these subjective evaluations. In each test REVLON REALISTIC® (NaOH relaxer) served as the source of irritation. These data show that the complete #407 product was as effective as petrolatum for preventing irritation. It further shows that dioctyl maleate or mineral oil alone did not provide the same degree of protection as was provided by #407. Although these data are subjective in nature they do reinforce observations made in earlier trials of #407 on the scalp.

TABLE 2

EVALUATION OF VARIOUS PRETREATMENTS FOR PREVENTING SKIN IRRITATION[a]

| Sample | | Elapsed time before, min | | | |
|---|---|---|---|---|---|
| TA040 | Pretreatment | Itching[b] | Stinging[b] | Burning[b] | Premature removal[b] |
| −012 | #407 | —[c] | — | — | — |
| | vs | | | | |
| | Revlon Realistic ® | 4.0 | 6.0 | 11.0 | 18.0 |
| −014 | Mineral Oil | 15.0 | 20.0 | — | — |

TABLE 2-continued

EVALUATION OF VARIOUS PRETREATMENTS FOR PREVENTING SKIN IRRITATION[a]

| Sample TA040 | Pretreatment | Elapsed time before, min | | | |
|---|---|---|---|---|---|
| | | Itching[b] | Stinging[b] | Burning[b] | Premature removal[b] |
| | vs Petrolatum | — | — | — | — |
| −028 | Dioctyl Maleate vs | 4.0 | 8.0 | 10.0 | 12.0 |
| | Cetiol HE ®[d] | 16.0 | 22.0 | 27.0 | 29.0 |
| −029 | Dioctyl Maleate vs | 9.0 | 11.0 | 29.0 | — |
| | Finsolv TN ®[d] | 13.0 | 15.0 | 29.0 | — |

[a]The data given in this table represent the subjective evaluation of barrier products by one individual. (Tony R. Adair). Pre-treatment was applied to the forearm prior to the application of relaxer. The source of irritation used for this study was REVLON REALISTIC ® (Regular) Lye Relaxer. Times given here represent the time elapsed between application of the relaxer and the advent of the designated sensation.
[b]For this test itching was defined as a sensation in which the subject feels the need to scratch the affected area. Stinging was defined as a sensation similar to an insect bite. Burning was defined as the sensation of having a hot object in contact with the skin. The maximum length of time the relaxer could remain in contact with the skin was 30 min. The time given here signifies an early removal of the product because of extreme discomfort.
[c]"—" means that this aspect of the test was not noted during the 30-min test period.
[d]CETIOL HE ® is a product, Henkel Corp. (Hoboken, NJ). The CTFA Dictionary defines CETIOL HE ® as the polyethylene glycol ether of glyceryl cocoate. FINSOLV. TN ® a product of Finetex, Inc. (Elmwood Park, NJ). The CTFA Dictionary defines FINSOLV TN ® as $C_{12}$–$C_{15}$ alkyl benzoate.

EXAMPLE 8

Table 3 contains data comparing the effects of various barrier products on the relaxation of hair. These data were obtained by coating approximately 2.0 g of negroid kinky hair with 1.0 g of the designated barrier product and subsequently relaxing the hair for 20 min. After neutralization each swatch was evaluated for "perceived straightness". The swatches were ranked in order from most straight to least straight. Both wet and dry evaluations were obtained in this manner. These data show that each of the barrier products has some negative effect on the efficiency of the relaxer treatment. Each of the swatches pretreated with a barrier product were subjectively judged to be less straight than the relaxed-only control. In both wet and dry evaluations of these swatches, petrolatum was consistently ranked as having most inhibited the relaxation of the hair. The rank ordering of the swatches between the relaxed-only control and those pretreated with petrolatum tended to vary between participants. This variation was expected because the differences in these swatches was minor.

TABLE 3

EFFECTS OF VARIOUS BARRIER PRODUCTS ON THE RELAXATION OF HAIR[a]

| Evaluation provided by: | Ranking of relaxation[b] | |
|---|---|---|
| | Wet hair | Dry hair |
| L.B. | Control[c] | Control |
| | #407 | Dioctyl maleate |
| | Mineral oil | #407 |
| | Dioctyl maleate | Mineral oil |
| | Petrolatum | Petrolatum |
| A.E. | Control | Control |
| | #407 | Dioctyl maleate |
| | Mineral oil | #407 |
| | Dioctyl maleate | Mineral oil |
| | Petrolatum | Petrolatum |
| T.A. | Control | Control |
| | #407 | Dioctyl maleate |
| | Mineral oil | Mineral oil |
| | Dioctyl maleate | #407 |
| | Petrolatum | Petrolatum |

[a]Kinky hair from DeMeo was pretreated with an amount of the designated barrier material equal to one-half the weight of the swatch. Each swatch was then relaxed for 20 min with D/L 2000 (RD099).
[b]Each participant was asked to rank the swatches in the order of MOST straight to LEAST straight. The swatches are arranged in this table in descending order.
[c]Represents relaxed hair which received no pre-treatment.

EXAMPLE 9

Procedure for Evaluating Barrier Products on Hair

Purpose: To determine the effects of various barrier-type formulations on the relaxation of hair.

Procedure:
1. Make tresses of kinky hair (about 6 inches long). Each tress should weigh approximately 0.759.
2. Apply barrier product to be tested at a rate which is approximately twice the weight of the hair used to prepare the tress.
3. Mix relaxer base with Activator cream and allow mixture to stand for 5 min.
4. Hang hair by proximal end and apply relaxer to the entire length of the tress. Apply the relaxer gently with fingertips, being sure not to rub hair in a fashion which will remove the barrier product.
5. Place a 2-oz weight on distal end of each swatch.
6. Leave weights in place for the duration of the relaxer treatment (7.5 min). Neutralize each tress with the appropriate neutralizing shampoo.
7. Attach each tress loosely to a glass rod with cotton thread and dry with a hair dryer for 1 hr (cool setting).
8. Remove tresses from a glass rods. Attach the bound end of the relaxed swatches to alligator clips positioned at the zero line on a finely divided graph paper. Stand graphs in a vertical position and equilibrate to room temperature and 65% RH for 1 hr.
9. Attach a pressure sensitive label to the hair so that the upper edge of the label marks a point that is 10 to 15 cm from the bottom of the tape that binds the swatch. Record the point as your initial length (Lr).
10. Allowing the label to hold the hairs together, pull the hair gently until it is fully extended but not stretched. Record this as the extended length (Ls) (marked at upper edge of label).
11. Cut the hair along the upper edge of the label.
12. Place chart in a vertical position in a constant humidity chamber maintained at 90% RH for 24 hr.
13. After 24 hr remove the chart assembly from the humidity chamber and allow tresses to equilibrate to room temperature and 65% RH for 1 hr.
14. Record the length of each switch (Lc) without touching the hair.

Calculations:

$$\% \text{ Relaxation} = 100\left(1 - \frac{Ls - Lr}{Ls}\right)$$

where  Ls = extended length
       Lr = initial length (3 or 6 cm)

$$\% \text{ Reversion} = \left[\% \text{ relaxation} - \left(100\left(1 - \frac{Ls - Lc}{Ls}\right)\right)\right]$$

where  Ls = initial extended length
       Lc = length after reversion

TABLE 4

RELAXATION STUDIES FOR HAIR TREATED WITH VARIOUS BARRIER PRODUCTS

| Sample TA044 | Barrier[a] product | Relaxation | Reversion |
|---|---|---|---|
| −012-02 | None | 98.82 ± 0.40 | 2.15 ± 1.23 |
| −012-05 | Petrolatum | 94.39 ± 0.97 | 4.86 ± 1.38 |
| −012-08 | Mineral oil (100%) | 98.82 ± 0.40 | 0.73 ± 0.72 |
| −012-14 | #407 | 97.67 ± 0.39 | 2.43 ± 2.29 |
| −012-20 | Mineral oil (87.5%) DOM[d] (12.5%) | 98.59 ± 0.00 | 0.97 ± 0.84 |
| −012-23 | Mineral Oil (50%) DOM (50%) | 98.82 ± 0.40 | 0.002 ± 0.01 |
| −012-26 | FINSOLV TN ® (90%) Petrolatum (10%) | 98.59 ± 0.00 | 0.00 ± 0.00 |

[a]Barrier product was applied to the hair in an amount equivalent to twice the-weight of the hair used in the tress. Relaxer was applied on top of the barrier product. Relaxation time was 7.5 min. See TA011-011 for procedure.
[b]Procedure given on TA011-011.
[d]DOM stands for dioctyl maleate (Bernel Ester DOM).
[c]FINSOLV TN ® is the tradename for the dioctyl maleate manufactured by Finetex, Inc.

EXAMPLE 10

Process

All tresses were taken from the same bundle of hair from DeMeo Brothers. Each tress was combed to remove any stray strands before the relaxation process. The protective gel vas applied to the tresses and allowed to sit 3 minutes before relaxer application. Tresses were relaxed with batch #RD102 FAILSAFE ® (plus strength) (GuanidineOH relaxer). The relaxer base was mixed with the cream activator and allowed to sit 10 minutes before applying to tresses. Processing time was 15 minutes. Each tress was neutralized with the amphoteric shampoo 3 times at 30 second. Tresses were allowed to air dry approximately 15 hours. Each tress was reweighed to determine the amount of protective gel left on hair.

TABLE 5

Evaluation of Protective Gels with FAILSAFE ® Relaxer Cream 15 - minutes relaxation time

| Tress No. | Init. wt. | wt. w/clamp | wt. after combed | wt. w/gel | COHW | wt. after drying | COHD |
|---|---|---|---|---|---|---|---|
| 1 | 2.58 | 2.71 | 2.09 | — | — | — | — |
| 2 | 2.59 | 2.88 | 2.24 | 3.65 PRECARE | S | 2.26 | S |
| 3 | 2.53 | 2.72 | 2.15 | 2.91 #407 | S | 2.12 | S |
| 4 | 2.58 | 2.73 | 2.00 | 2.87 75% oil 25% DOM | S | 2.19 | S |
| 5 | 2.58 | 2.82 | 2.25 | 3.45 25% oil 75% DOM | S | 2.19 | S |
| 6 | 2.55 | 2.80 | 2.23 | — | S | 2.19 | S |

Codes: S = straight
COHW = condition of hair wet
COHD = condition of hair dry

EXAMPLE 11

The Procedure was repeated changing the relaxation time from 15 minutes to 5 minutes. The results are as follow:

TABLE 6

Evaluation of Protective Gel with FAILSAFE ® Relaxer Cream 5-min relaxation time

| Tress No. | Init. wt. | wt. w/clamp | wt. after combed | wt. w/gel | COHW | wt. after drying | COHD |
|---|---|---|---|---|---|---|---|
| 8 | 2.59 | 2.84 | 2.57 | 3.08 Petrolatum | VW | 2.23 | W |

TABLE 6-continued

Evaluation of Protective Gel with FAILSAFE ® Relaxer Cream 5-min relaxation time

| Tress No. | Init. wt. | wt. w/clamp | wt. after combed | wt. w/gel | COHW | wt. after drying | COHD |
|---|---|---|---|---|---|---|---|
| 9 | 2.56 | 2.83 | 2.20 | 2.90 MINERAL OIL | W | 2.28 | W |
| 10 | 2.52 | 2.78 | 2.22 | 3.00 #407 | W | 2.19 | W |

Codes:
VW = VERY WAVY
W = WAVY
SW = SLIGHTLY WAVY
* = REPEAT

The percent relaxation was calculated for each tress. The results are as follows:

TABLE 7

| TRESS NO. | % RELAXATION INITIAL ($L_R$) | EXTENDED ($L_S$) | % RELAXATION |
|---|---|---|---|
| 8 (PETROLATUM) | 11.0 | 13.0 | 84.46 |
| 9 (MINERAL OIL) | 12.0 | 13.0 | 92.31 |
| 10 (#407) | 10.0 | 10.6 | 94.34 |

What is claimed is:

1. A method of protecting skin and scalp from the irritating side effects of hair relaxers without interfering with the hair straightening action of hair relaxers, said method comprising applying to a user's scalp, prior to the application of the hair relaxer, a protection-effective amount of a composition comprising:
   a) about 10-85 weight percent parrafin; and
   b) about 15-90 weight percent of at least one ester, wherein the ester is of the formula:

$R_1-(COO)-[X-(COO)]_n-R_2$, wherein n is 0, 1, or 2;
   wherein $R_1$ is selected from the group consisting of $C_1-C_{30}$ alkyl, $C_1-C_{30}$ alkene, phenyl, benzyl, polyhydroxy $C_1-C_{30}$ alkanols, $C_1-C_5$ amino acid, $C_1-C_{30}$ alkyl-amine, and $C_1-C_{30}$ oxy-alcohol;
   wherein x is selected from the group consisting of a single bond, $C_1-C_{30}$ alkyl, $C_1-C_{30}$ alkene, $C_1-C_{30}$ alkyl-oxy $C_1-C_{30}$ alkyl, $C_1-C_{30}$ alkyl-carboxy $C_1-C_{30}$ alkyl, phenyl, and phenyl $C_1-C_{30}$ alkyl; and
   wherein $R_2$ is defined the same as $R_1$, and $R_1$ and $R_2$ may be the same or may be different.

2. A method of relaxing hair without irritating the skin and scalp which comprises applying a protection-effective amount of a composition comprising:
   a) about 10-85 weight percent parrafin; and
   b) about 15-90 weight percent of at least one ester, wherein the ester is of the formula:

$R_1-(COO)-[X-(COO)]_n-R_2$, wherein n is 0, 1, or 2;
   wherein $R_1$ is selected from the group consisting of $C_1-C_{30}$ alkyl, $C_1-C_{30}$ alkene, phenyl, benzyl, polyhydroxy $C_1-C_{30}$ alkanols, $C_1-C_5$ amino acid, $C_1-C_{30}$ alkyl-amine, and $C_1-C_{30}$ oxy-alcohol;
   wherein x is selected from the group consisting of a single bond, $C_1-C_{30}$ alkyl, $C_1-C_{30}$ alkene, $C_1-C_{30}$ alkyl-oxy $C_1-C_{30}$ alkyl, $C_1-C_{30}$ alkyl-carboxy $C_1-C_{30}$ alkyl, phenyl, and phenyl $C_1-C_{30}$ alkyl; and
   wherein $R_2$ is defined the same as $R_1$, and $R_1$ and $R_2$ may be the same or may be different, to a user's scalp, and then applying a hair relaxer to the user's hair.

* * * * *